United States Patent [19]
Christensen et al.

[11] Patent Number: 6,146,865
[45] Date of Patent: Nov. 14, 2000

[54] NUCLEIC ACIDS ENCODING POLYPEPTIDES HAVING PYRANOSE OXIDASE ACTIVITY

[75] Inventors: Soren Christensen; Soren Flensted Lassen, both of Copenhagen; Palle Schneider, Ballerup, all of Denmark

[73] Assignee: Novo Nordisk A/S, Bagsvaerd, Denmark

[21] Appl. No.: 09/305,381

[22] Filed: May 5, 1999

Related U.S. Application Data

[60] Provisional application No. 60/088,724, Jun. 10, 1998.

[30] Foreign Application Priority Data

Jun. 8, 1998 [DK] Denmark .............................. 1998 00774

[51] Int. Cl.⁷ ............................... C12N 9/04; C12N 1/20; C12N 15/00; C12N 5/00; C07H 21/04

[52] U.S. Cl. ................. 435/190; 435/252.3; 435/252.31; 435/325; 435/320.1; 435/6; 536/23.2

[58] Field of Search ................................ 435/190, 320.1, 435/252.3, 325, 252.31, 6; 536/23.2

*Primary Examiner*—Rebecca E. Prouty
*Assistant Examiner*—M. Monshipouri
*Attorney, Agent, or Firm*—Steve T. Zelson; Elias J. Lambiris; Carol E. Rozek

[57] ABSTRACT

The present invention relates to isolated nucleic acid sequences encoding polypeptides having pyranose oxidase activity. The invention also relates to nucleic acid constructs, vectors and host cells containing the nucleic acid sequences as well as recombinant methods for producing the polypeptides.

16 Claims, 3 Drawing Sheets

FIG 1A

```
CAAGGCTGCGAAGAGGGCCACTGCGCATTCTCTCCCGGCGCTGCCTGGTCCCGGCGACCTGCCGCCGGGCCCGGGCATGAA
 K  A  K  R  A  T  A  H  S  L  P  P  L  P  P  G  P  L  P  P  G  M  N
GCCATGTTCGAGATTGGAGAGATCGACTCGGCTTGAAGATCGGCTCACACAAGAAGAACACCGTCGAGTACCAG
 A  M  F  E  I  G  E  I  D  S  G  L  K  I  G  S  H  K  K  N  T  V  E  Y  Q
TAAGCCCGGCGTCATGGCAAGCTTCGACGTTCTTCGTCCGCAACGGGGCGAATCCAGAGCAAGACCCGCTGCGCA
 L  S  P  A  S  W  Q  A  S  T  F  F  V  R  N  G  A  N  P  E  Q  D  P  L  R
GCGCCCGCTGCTCGTGAAGAACGACTCCAAGGCGGACGACGCCGAGTGGGACAGGCTCTACAAGAAGGCCGAGTC
 R  D  F  Q  Q  I  P  L  A  A  T  R  Q  S  P  T  F  V  E  W  S  S  A  H
GTGGCGGACTTCCAGCAGATCCCGCTCGCGGCGACAGAGCCGCCAGAGCCCGACGTTCGTCGAGTGGAGCTCGGCGCAC
 R  D  F  Q  Q  I  P  L  A  A  T  R  Q  S  P  T  F  V  E  W  S  S  A  H
TGAGGGCGATAACGCGAACTCGGAGATCGTAGGCCTGGATGTCCGCGACCTCCACGGGGGCAAGAGCATCACCA
 *  G  D  N  A  N  S  E  I  V  G  L  D  V  R  D  L  H  G  G  K  S  I  T
TCCCGACCCCGCCAAGCCGCTGCCGTCTCTGCCGTACCTGGGAACCAAGACAACAAGCACCCGGACTGGTGGAACGAGAGAAGGTGAAGAAGCACATG
 P  D  P  A  K  P  L  P  S  L  P  Y  L  G  T  H  I  T  E  Q  T  L  V  F
AGCGTCACGTATACCCCCGGGCAACAACCCGAACAACAAGCACCCGGACTGGTGGAACGAGAAGGTGAAGAAGCACATG
 V  T  Y  T  P  G  N  N  P  N  N  K  H  P  D  W  W  N  E  K  V  K  K  H  M
GGCACACACCCAGATTCACCGGCAGCTACGGCGCCGTGCAGCAGAGCATCGACTCGCGGCTCATCGTCG
 T  Q  I  H  R  D  A  F  S  Y  G  A  V  Q  Q  S  I  D  S  R  L  I
GCAGCCGACGTTCGACGAGAGGGCGGAAGCGGACAAGTGTGCGCGGTGACAAGATGATGACCGACATGTGCGTCATGTC
 Q  P  T  F  D  F  F  R  F  P  P  G  R  E  A  E  D  M  M  T  D  M  C  V  M  S
ATGGGCTTCGACGAGAAGGCGGACAAGTGTGCGCGGTGACAAGATGATGACCGACATGTGCGTCATGTC
 G  F  D  E  K  A  D  K  C  C  V  D  T  D  S  R  V  F  G  F  F  K  N  L  F
ACATCAAGAAGAACTTCGAGCCCGAGCCCGAACCCCGTGAAGCACCACAACTGATGCGTTGCTTCGATGTCATTG
 I  K  K  N  F  E  P  S  P  N  P  V  K  H  H  N  *
GTTTATGTGTACGAGTAGTCGCAATCTGCATATCTGACGTTTGAGCCTTTGAAAAAAAAAAAAAAAATTC
```

*FIG 1B*

| | | | |
|---|---|---|---|
| PROD C. Versicolor | 1 | MSTSSSDPFFNFTKSSFRSAAAQKASATSLPPLPGPDKKVPGMDIKYDVVIVGSGPIGCTY | 61 |
| PROD T. Hirsuta | 1 | MSASSSDPFHSFAKTSFTSKAAKRATAHSLPPLPGPGDLPPGMNVEYDVAIVGSGPIGCTY | 61 |
| PROD C. Versicolor | 62 | ARELVEAGYKVAMFDIGEIDSGLKIGAHKKNTVEYQKNIDKFVNVIQGQLMSVSVPVNTLV | 122 |
| PROD T. Hirsuta | 62 | ARELVEAGFNVAMFEIGEIDSGLKIGSHKKNTVEYQKNIDKFVNVIQGQLMPVSVPVNTMV | 122 |
| PROD C. Versicolor | 123 | IDTLSPTSWQASSFFVRNGSNPEQDPLRNLSGQAVTRVVGGMSTHWTCATPRFDREQRPLL | 183 |
| PROD T. Hirsuta | 123 | VDTLSPASWQASTFFVRNGANPEQDPLRNLSGQAVTRVVGGMSTHWTCATPRFEKLQRPLL | 183 |
| PROD C. Versicolor | 184 | VKDDQDADDAEWDRLYTKAESYFKTGTDQFKESIRHNLVLNKLAEEYKGQRDFQQIPLAAT | 244 |
| PROD T. Hirsuta | 184 | VKNDSKADDAEWDRLYKKAESYFKTGTTQFAESIRHNLVLVKKLQEEYKGVRDFQQIPLAAT | 244 |
| PROD C. Versicolor | 245 | RRSPTFVEWSSANTVFDLQNRPNTDAPNERFNLFPAVACERVVRNTSNSEIESLHIHDLIS | 305 |
| PROD T. Hirsuta | 245 | RQSPTFVEWSSAHTVFDLENRPNKDAPKQRFNLFPAVACTNVRRDNANSEIVGLDVRDLHG | 305 |
| PROD C. Versicolor | 306 | GDRFEIKADVFVLTAGAVHNAQLLVNSGFGQLGRPDPANP-PQLLPSLGSYITEQSLVFCQ | 365 |
| PROD T. Hirsuta | 306 | GKSITIKAKVYILTAGAVHNAQLLAASGFGQLGRPDPAKPLPSLLPYLGTHITEQTLVFCQ | 366 |
| PROD C. Versicolor | 366 | TVMSTELIDSVKSDMIIRGNPGDLGYSVTYTPGAETNKHPDWWNEKVKNHMMQHQEDPLPI | 426 |
| PROD T. Hirsuta | 367 | TVMSTELINSVTADMTIVGKPGHPDYSVTYTPGNPNNKHPDWWNEKVKKHMMDHQEDPLPI | 427 |
| PROD C. Versicolor | 427 | PFEDPEPQVTTLFQPSHPWHTQIHRDAFSYGAVQQSIDSRLIVDWRFFGRTEPKEENKLWF | 487 |
| PROD T. Hirsuta | 428 | PFEDPEPQVTTLFQATHPWHTQIHRDAFSYGAVQQSIDSRLIVDWRFFGRTEPKEENKLWF | 488 |
| PROD C. Versicolor | 488 | SDKITDTYNMPQPTFDFRFPAGRTSKEAEDMMTDMCVMSAKIGGFLPGSLPQFMEPGLVLH | 548 |
| PROD T. Hirsuta | 489 | SDKITDAYNLRQPTFDFRFPGGR---EAEDMMTDMCVMSAKIGGFLPGSYPQFMEPGLVLH | 546 |
| PROD C. Versicolor | 549 | LGGTHRMGFDEQEDKCCVNTDSRVFGFKNLFLGGCNIPTAYGANPTLTAMSLAIKSCEYI | 609 |
| PROD T. Hirsuta | 547 | LGGTHRMGFDEKADKCCVDTDSRVFGFKNLFLGGCNIPTAYAANPTLTAMSLAIKSCEYI | 607 |
| PROD C. Versicolor | 610 | KNNFTPSPFTDQAE- | 623 |
| PROD T. Hirsuta | 608 | KKNFEPSPNPVKHHN | 622 |

FIG 2

NUCLEIC ACIDS ENCODING POLYPEPTIDES HAVING PYRANOSE OXIDASE ACTIVITY

CROSS-REFERENCE TO RELATED APPLICATIONS

This application claims priority under 35 U.S.C. 119 of U.S. provisional application No. 60/088,724 filed Jun. 10, 1998 and Danish application no. PA 1998 00774 filed Jun. 8, 1998, the contents of which are fully incorporated herein by reference.

BACKGROUND OF THE INVENTION

1. Field of the Invention

The present invention relates to isolated nucleic acid sequences encoding polypeptides having pyranose oxidase activity. The invention also relates to nucleic acid constructs, vectors, and host cells comprising the nucleic acid sequences as well as recombinant methods for producing the polypeptides.

2. Description of the Related Art

Pyranose oxidases (E.C.1.1.3.10) are flavoproteins which catalyze the oxidation of several monosaccharides in the pyranose form at position C2 to produce 2-keto derivatives with the concomitant release of hydrogen peroxide. D-glucose, in its pyranose form, tends to be the preferred substrate, and is converted to 2-keto-D-glucose by pyranose oxidase. A number of other substrates can also be oxidized by the enzyme, e.g., xylose and L-sorbose which are converted to 2-keto-D-xylose and 5-keto-D-fructose, respectively. The pyranose oxidase is distinct from glucose oxidase (E.C.1.1.3.4) which catalyzes the oxidation of β-D-glucose at position C1 to form D-glucono-1,5-lactone and hydrogen peroxide.

Pyranose oxidases are of widespread occurrence, but in particular, in Basidiomycota (Basidiomycete) fungi. Pyranose oxidases have been characterized or isolated, e.g., from the following sources: *Peniophora gigantea*, genera of the Aphyllophorales order, *Phanerochaete chrysosporium*, *Polyporus* spp., and *Bierkandera adusta* and *Phlebiopsis gigantea*. The use in baking of a pyranose oxidase from *Trametes hirsuta* is disclosed in WO 97/22257 (Novo Nordisk A/S) and in JP 9098710 A (Oriental Yeast Co.). DE 195 45 780 A1 (Kikkoman Corp.) discloses the DNA sequence encoding an enyzme with pyranose oxidase activity at neutral pH from a strain of *Coriolus versicolor*.

It is an object of the present invention to provide isolated nucleic acid sequences encoding polypeptides having pyranose oxidase activity.

SUMMARY OF THE INVENTION

The present invention relates to isolated nucleic acid sequences encoding polypeptides having pyranose oxidase activity, selected from the group consisting of:

(a) a nucleic acid sequence having at least 85% homology with the nucleic acid sequence of SEQ ID NO:1;
(b) a nucleic acid sequence encoding a polypeptide having an amino acid sequence which has at least 85% identity with the amino acid sequence of SEQ ID NO:2;
(c) a nucleic acid sequence which hybridizes under high stringency conditions with (i) the nucleic acid sequence of SEQ ID NO:1, or (ii) its complementary strand;
(d) an allelic variant of (a), (b), or (c); and
(e) a subsequence of (a), (b), (c), or (d), wherein the subsequence encodes a polypeptide fragment which has pyranose oxidase activity.

The present invention also relates to nucleic acid constructs, vectors, and host cells comprising the nucleic acid sequences as well as recombinant methods for producing the polypeptide.

BRIEF DESCRIPTION OF THE DRAWINGS

FIG. 1 shows the nucleic acid sequence and the deduced amino acid sequence of a *Trametes hirsuta* pyranose oxidase contained in DSM 12119 (SEQ ID NOS:1 and 2, respectively). The N-terminal amino acid sequence obtained as described in Example 3 is underscored with a dotted line and the restriction sites used for cDNA cloning are underlined.

FIG. 2 shows an alignment of the deduced amino acid sequences of the pyranose oxidases, PROD, from *Coriolus versicolor* and *Trametes hirsuta*. Identical residues are highlighted in grey.

DETAILED DESCRIPTION OF THE INVENTION

Polypeptides Having Pyranose Oxidase Activity

The term "pyranose oxidase activity" is defined herein as an oxidation in which $O_2$ is an acceptor and the substrate is C2 of the pyranose form of a monosaccharide, resulting in its conversion to the corresponding dicarbonyl sugar and hydrogen peroxide. Monosaccharide substrates include D-xylose, L-sorbose and D-glucose, with D-glucose being the preferred substrate.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In a first embodiment, the present invention relates to isolated nucleic acid sequences encoding polypeptides having an amino acid sequence which has a degree of identity to the amino acid sequence of SEQ ID NO:2 of at least about 85%, more preferably at least about 90%, most preferably at least about 95%, and even most preferably at least about 97%, which have pyranose oxidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., U.S.A. 53711) (Needleman, S. B. and Wunsch, C. D., (1970), Journal of Molecular Biology, 48, 443–45), using GAP with the following settings for polypeptide sequence comparison: GAP creation penalty of 3.0 and GAP extension penalty of 0.1.

Preferably, the nucleic acid sequences of the present invention encode polypeptides which comprise the amino acid sequence of SEQ ID NO:2, or an allelic variant thereof. In a more preferred embodiment, the nucleic acid sequences of the present invention encode polypeptides which comprise the amino acid sequence of SEQ ID NO:2. In another preferred embodiment, the nucleic acid sequences of the present invention encode a polypeptide which has the amino acid sequence of SEQ ID NO:2 or a fragment thereof, wherein the fragment has pyranose oxidase activity. A fragment of SEQ ID NO:2 is a polypeptide having one or more amino acids deleted from the amino and/or carboxy terminus of this amino acid sequence. In a most preferred embodiment, the nucleic acid sequence encodes a polypeptide which has the amino acid sequence of SEQ ID NO:2. The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 which has pyranose oxidase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 15 nucleotides.

An allelic variant denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant of a polypeptide is a polypeptide encoded by an allelic variant of a gene.

The amino acid sequences of the homologous polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic is acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated nucleic acid sequences which are homologous to SEQ ID NO:1, with a degree of identity to the nucleic acid sequence of SEQ ID NO:1 of at least about 85%, more preferably about 90%, even more preferably about 95%, and most preferably about 97% identity, which encode a polypeptide having pyranose oxidase activity; or allelic variants and subsequences of SEQ ID NO:1 which encode polypeptide fragments which have pyranose oxidase activity. For purposes of the present invention, the degree of homology between two nucleic acid sequences is determined by the GAP provided in the GCG software program package (supra) with the following settings for nucleotide sequence comparison: GAP creation penalty of 5.0 and GAP extension penalty of 0.3.

In a third embodiment, the present invention relates to isolated nucleic acid sequences encoding polypeptides having pyranose oxidase activity which hybridize under low stringency conditions, more preferably medium stringency conditions, and most preferably high stringency conditions, with an oligonucleotide probe which hybridizes under the same conditions with the nucleic acid sequence of SEQ ID NO:1 or its complementary strand (J. Sambrook, E. F. Fritsch, and T. Maniatus, 1989, *Molecular Cloning, A Laboratory Manual*, 2d edition, Cold Spring Harbor, N.Y.); or allelic variants and subsequences of SEQ ID NO:1 which encode polypeptide fragments which have pyranose oxidase activity.

Hybridization indicates that by methods of standard Southern blotting procedures, the nucleic acid sequence hybridizes to the oligonucleotide probe corresponding to the polypeptide encoding part of the nucleic acid sequence shown in SEQ ID NO:1, under low to high stringency conditions (i.e., prehybridization and hybridization at 42° C. in 5X SSPE, 0.3% SDS, 200 $\mu$g/ml sheared and denatured salmon sperm DNA, and either 25, 35 or 50% formamide for low, medium and high stringencies, respectively). In order to identify a clone or DNA which is homologous with SEQ ID NO:1, the hybridization reaction is washed three times for 30 minutes each using 2xSSC, 0.2% SDS preferably at least 50° C., more preferably at least 55° C., more preferably at least 60° C., more preferably at least 65° C., even more preferably at least 70° C., and most preferably at least 75° C.

The nucleic acid sequence of SEQ ID NO:1, or a subsequence thereof, as well as the amino acid sequence of SEQ ID NO:2, or a partial sequence thereof, may be used to design an oligonucleotide probe to identify and clone DNA encoding polypeptides having pyranose oxidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). For example, molecules to which a $^{32}$P-, $^{3}$H- or $^{35}$S-labelled oligonucleotide probe hybridizes may be detected by use of X-ray film.

Thus, a genomic, cDNA or combinatorial chemical library prepared from such other organisms may be screened for DNA which hybridizes with the probes described above and which encodes a polypeptide having pyranose oxidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. A clone or DNA which is homologous to SEQ ID NO:1 may then be identified following standard Southern blotting procedures.

In a fourth embodiment, the present invention relates to isolated nucleic acid sequences encoding polypeptides with pyranose oxidase activity having the following physico-chemical properties: activity at a pH optimum of about 6 and a temperature optimum of about 40° C., and pH stability between 3 and 9 and a temperature stability up to 55° C.

The nucleic acid sequences of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted.

The nucleic acid sequences may be obtained from a bacterial source. For example, these polypeptides may be obtained from a bacterium such as a Bacillus strain, e.g., *Bacillus brevis, Bacillus pumilus, Bacillus migulanus* or *Bacillus mojavensis*; or a strain of Pseudomonas, e.g., *Pseudomonas aureofaciens*; or a strain of Paenibacillus, e.g., *Paenibacillus polymyxa*; or a strain of Ralstonia, e.g., *Ralstonia pickettii*; or a strain of Alteromonas, e.g., *Alteromonas macleodii*; or a strain of Nigrospora sp.

The nucleic acid sequences may be obtained from a fungal source, and more preferably from a strain such as a Basidiomycota, Ascomycota or Chytridiomycota strain.

A preferred Basidiomycota strain is a strain such as one classified as one of the following: Aphyllophorales, Coriolales, Schizophyllales, Stereales or Xenasmatales; in particular a strain belonging to one of the following families: Polyporaceae or Corticiaceae; in particular, a strain belonging to one of the following genera: Fusarium, Cordyceps, Allomyces, Pythium, Phytium, Apodachlya, Microdochium, Stromatinia, Saprolegnia, Laurilia, Punctularia, Trametes, Polyporus, Phanerochaete, Peniophora; in particular, a strain belonging to one of the following species: *Peniophora gigantea, Phanerochaete chrysosporium, Coriolus hirsutus, Trametes suaveolens, Trametes versicolor*, or *Trametes villosa*.

In another preferred embodiment, the nucleic acid sequence encodes a pyranose oxidase obtained from a strain selected from the group consisting of: *Fusarium equiseti*, Daldinia sp., Phoma sp., Sporormiella sp., Epicoccum sp., *Cordyceps militaris, Allomyces arbuscula, Pythium irregulare, Phytium intermedium, Phytium ultimum, Apodachlya punctata, Microdochium nivale, Stromatinia rapulum, Saprolegnia diclina, Trametes hirsuta, Laurilia sulcata* and *Punctularia stringoso-zonata*.

In another preferred embodiment, the nucleic acid sequence encodes a polypeptide obtained from Trametes, e.g., *Trametes hirsuta*, and in a more preferred embodiment, the nucleic acid sequence is the nucleic acid sequence set forth in SEQ ID NO:1. In another more preferred embodiment, the nucleic acid sequence is the sequence contained in plasmid pA2P.ox1 which is contained in *Escherichia coli* DSM 12119.

It will be understood that for the aforementioned species, the invention encompasses both the perfect and imperfect states, and synonyms or other taxonomic equivalents, e.g., anamorphs or teleomorphs, regardless of the species name by which they are known. Those skilled in the art will readily recognize the identity of appropriate equivalents. For example, the polypeptides may be obtained from microorganisms which are taxonomic equivalents of Trametes, regardless of the species name by which they are commonly known.

The taxonomic classification used herein builds primarily on the system used in the NIH Database (Entrez, version spring 1996) available on World Wide Web at http://www3.ncbi.nlm.nih.gov/htbin/ef/entrezTAX.

Classification of fungal organisms not included in the Entrez database may be found in the following reference books which are generally available and accepted in the art:

Ascomycetes: Eriksson, O. E. & Hawksworth, D. L.: *Systema Ascomycetum vol* 12 (1993);

Basidiomycetes: Jülich, W.: *Higher Taxa of Basidiomycetes*, Bibliotheca Mycologia 85, 485pp (1981); Hansen & Knudsen, Nordsvamp: *Nordic Macromycetes* (1997);

Zygomycetes: O'Donnell, K.: *Zygomycetes in Culture*, University of Georgia, U.S., 257pp (1979).

General mycological reference books include: Hawksworth, D. L., Kirk, P. M., Sutton, B. C. and Pegler, D. N. *Dictionary of the fungi*, International Mycological Institute (1995); and Von Arx, J. A. *The genera of fungi sporulating in culture* (1981), and Alexopoulos, Mims & Blackwell. *Introductory Mycology* (1996).

Other sources of taxonomic information may be found in *The Approved List of Bacterial Names*, Skerman, McGowan and Sneath, eds., American Society for Microbiology, 1989; and *Index of the Bacterial and Yeast Nomenclatural Changes*, American Society for Microbiology, 1989.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. (See, e.g., Innis et al., 1990, PCR: *A Guide to Methods and Application*, Academic Press, New York.) Other nucleic acid amplification procedures such as ligase chain reaction (LCR), ligated activated transcription (LAT) and nucleic acid sequence-based amplification (NASBA) may be used. The nucleic acid sequence may be cloned from a strain of Trametes, or another or related organism and thus, for example, may be an allelic or species variant of the polypeptide encoding region of the nucleic acid sequence.

Modification of a nucleic acid sequence of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for pyranose oxidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

A nucleic acid sequence of the present invention may also encode fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide having pyranose oxidase activity including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" as defined herein is a sequence which is transcribed into mRNA and translated into a polypeptide. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide may be manipulated in a variety of ways to provide for expression of the polypeptide having pyranose oxidase activity. Manipulation of the nucleic acid sequence prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for the expression of a polypeptide. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the nucleic acid sequence such that the control sequence directs the production of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (U.S. Pat. No. 4,288,627), and mutant, truncated, and hybrid promoters thereof. Particularly preferred promoters for use in filamentous fungal host cells are the TAKA amylase, NA2-tpi (a hybrid of the promoters from the genes encoding *Aspergillus niger* neutral alpha-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983–5990. Polyadenylation sequences are well known in the art for mammalian host cells.

The control sequence may also be a signal peptide coding region, which codes for an amino acid sequence linked to the amino terminus of a polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. The signal peptide coding region may be obtained from a glucoamylase or an amylase gene from an Aspergillus species, a lipase or proteinase gene from a Rhizomucor species, the gene for the alpha-factor from *Saccharomyces cerevisiae*, an amylase or a protease gene from a Bacillus species, or the calf preprochymosin gene. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, *Microbiological Reviews* 57: 109–137.

An effective signal peptide coding region for filamentous fungal host cells is the signal peptide coding region obtained from the *Aspergillus oryzae* TAKA amylase gene, *Aspergillus niger* neutral amylase gene, *Rhizomucor miehei* aspartic proteinase gene, *Humicola lanuginosa* cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of the polypeptide and the signal peptide region is positioned next to the amino terminus of the propeptide region.

The nucleic acid constructs of the present invention may also comprise one or more nucleic acid sequences which encode one or more factors that are advantageous for directing the expression of the polypeptide, e.g., a transcriptional activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

A transcriptional activator is a protein which activates transcription of a nucleic acid sequence encoding a polypeptide (Kudla et al., 1990, *EMBO Journal* 9: 1355–1364; Jarai and Buxton, 1994, *Current Genetics* 26: 2238–244; Verdier, 1990, *Yeast* 6: 271–297). The nucleic acid sequence encoding an activator may be obtained from the genes encoding *Bacillus stearothermophilus* NprA (nprA), *Saccharomyces cerevisiae* heme activator protein 1 (hap1), *Saccharomyces cerevisiae* galactose metabolizing protein 4 (gal4), *Aspergillus nidulans* ammonia regulation protein (areA), and *Aspergillus oryzae* alpha-amylase activator (amyR). For further examples, see Verdier, 1990, supra and MacKenzie et al., 1993, *Journal of General Microbiology* 139: 2295–2307.

A chaperone is a protein which assists another polypeptide in folding properly (Hartl et al., 1994, TIBS 19: 20–25; Bergeron et al., 1994, TIBS 19: 124–128; Demolder et al., 1994, *Journal of Biotechnology* 32: 179–189; Craig, 1993, *Science* 260: 1902–1903; Gething and Sambrook, 1992, *Nature* 355: 33–45; Puig and Gilbert, 1994, *Journal of Biological Chemistry* 269: 7764–7771; Wang and Tsou, 1993, *The FASEB Journal* 7: 1515– 11157; Robinson et al., 1994, *Bio/Technology* 1: 381–384; Jacobs et al., 1993, *Molecular Microbiology* 8: 957–966). The nucleic acid sequence encoding a chaperone may be obtained from the genes encoding *Bacillus subtilis* GroE proteins, *Bacillus subtilis* PrsA,*Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, *Yeast* 10: 67–79; Fuller et al., 1989, *Proceedings of the National Academy of Sciences USA* 86: 1434–1438; Julius et al., 1984, *Cell* 37: 1075–1089; Julius et al., 1983, *Cell* 32: 839-852; U.S. Pat. No. 5,702, 934). The nucleic acid sequence encoding a processing protease may be obtained from the genes encoding *Saccharomyces cerevisiae* dipeptidylaminopeptidase, *Saccharomyces cerevisiae* Kex2, *Yarrowia lipolytica* dibasic processing endoprotease (xpr6), and *Fusarium oxysporum* metalloprotease (p45 gene).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of a nucleic acid sequence of the present invention which is endogenous to a cell. The constructs may contain the minimal number of components necessary for altering expression of the endogenous nucleic acid sequence. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous nucleic acid sequence site. The targeting sequence directs the integration of elements (a)–(d) into the endogenous nucleic acid sequence such that elements (b)–(d) are operably linked to the endogenous nucleic acid sequence. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous nucleic acid sequence. However, the constructs may contain additional components such as a selectable marker.

In both embodiments, the introduction of these components results in production of a new transcription unit in which expression of the endogenous nucleic acid sequence is altered. In essence, the new transcription unit is a fusion product of the sequences introduced by the targeting constructs and the endogenous nucleic acid sequence. In one embodiment in which the endogenous nucleic acid sequence is altered, the nucleic acid sequence is activated. In this embodiment, homologous recombination is used to replace, disrupt, or disable the regulatory region normally associated with the endogenous nucleic acid sequence of a parent cell through the insertion of a regulatory sequence which causes the nucleic acid sequence to be expressed at higher levels than evident in the corresponding parent cell. The activated nucleic acid sequence can be further amplified by the inclusion of an amplifiable selectable marker gene in the construct using methods well known in the art (see, for example, U.S. Pat. No. 5,641,670). In another embodiment in which the endogenous nucleic acid sequence is altered, expression of the gene is reduced.

The targeting sequence can be within the endogenous nucleic acid sequence, immediately adjacent to the nucleic acid sequence, within an upstream gene, or upstream of and at a distance from the endogenous nucleic acid sequence. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous nucleic acid sequence. An exon is defined as a DNA sequence which is copied into RNA and is present in a mature mRNA molecule such that the exon sequence is in-frame with the coding region of the endogenous nucleic acid sequence. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous nucleic acid sequence so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG genes of *Aspergillus nidulans* or *Aspergillus oryzae* and the bar gene of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to amplify expression of the nucelic acid sequence. Stable amplification of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by culturing the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

A vector comprising a nucleic acid sequence of the present invention is introduced into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulars, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. The introduction of a vector into a bacterial host cell may, for instance, be effected by protoplast transformation (see, e.g., Chang and Cohen, 1979, *Molecular General Genetics* 168: 111–115), by using competent cells (see, e.g., Young and Spizizin, 1961, *Journal of Bacteriology* 81: 823–829, or Dubnau and Davidoff-Abelson, 1971, *Journal of Molecular Biology* 56: 209–221), by electroporation (see, e.g., Shigekawa and Dower, 1988, *Biotechniques* 6: 742–751), or by conjugation (see, e.g., Koehler and Thorne, 1987, *Journal of Bacteriology* 169: 5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed below. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Kluyveromyces, Pichia, and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; and *The Molecular Biology of the Yeast Saccharomyces*, Strathern et al., editors, 1981).

In an even more preferred embodiment, the yeast host cell is a cell of a species of Candida, Kluyveromyces, Pichia, Saccharomyces, Schizosaccharomyces, or Yarrowia.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum* cell. In an even most preferred embodiment, the filamentous fungal parent cell is a *Fusarium venenatum* (Nirenberg sp. nov.). In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. A suitable method of transforming Fusarium species is described by Malardier et al., 1989, Gene 78: 147–156 or in WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920. Mammalian cells may be transformed by direct uptake using the calcium phosphate precipitation method of Graham and Van der Eb (1978, *Virology* 52: 546).

Methods of Production

The present invention also relates to methods for producing a polypeptide comprising (a) cultivating a host cell under conditions suitable for production of the polypeptide; and (b) recovering the polypeptide.

The present invention further relates to methods for producing a polypeptide comprising (a) cultivating a homologously recombinant cell, having incorporated therein a new transcription unit comprising a regulatory sequence, an exon, and/or a splice donor site operably linked to a second exon of a nucleic acid sequence of the present invention which is endogenous to a cell, under conditions suitable for production of the polypeptide encoded by the endogenous nucleic acid sequence; and (b) recovering the polypeptide. The methods are based on the use of gene activation technology, for example, as described in U.S. Pat. No. 5,641,670. Gene activation technology is based on activating a gene which is normally unexpressed in a cell or increasing expression of a gene which is expressed at very low levels in a cell. Gene activation technology includes methods of inserting an exogenous DNA construct containing a regulatory sequence, an exon, and/or a splice donor site into the genomic DNA of a cell in such a manner that the insertion results in the production of a new transcription unit in which the regulatory sequence, the exon, and/or the splice donor site are operably linked to and activate expression of the endogenous nucleic acid sequence.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, CA, 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining pyranose oxidase activity are known in the art and include, e.g., *Methods in Enzymology* (1988) 161: 316–322 and *Appl. Microbiol.* Biotechnol. (1997) 47: 508–514.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), SDS-PAGE, or extraction (see, e.g., *Protein Purification*, J.-C. Janson and Lars Ryden, editors, VCH Publishers, New York, 1989).

The present invention is further described by the following examples which should not be construed as limiting the scope of the invention.

EXAMPLES

Materials

Chemicals used as buffers and substrates are commercial products of at least reagent grade.

Example 1

Purification of *Trametes hirsuta* Pyranose Oxidase

Pyranose oxidase was purified from 5700 ml of fermentation broth in which a strain of *Trametes hirsuta*, CBS 122.96, was cultured in a medium comprised of carbon and nitrogen sources and trace metals. The collected broth was filtered through a Seitz EKS (Seitz-Filter-Werke GmbH und Co., Bad Kreuznach, DE) and concentrated to 640 ml by ultrafiltration using a filter with a molecular weight cutoff of 10 kDa (Filtron Technologoy Corp., Northborough Mass., U.S.). The enzyme was precipitated by adding $(NH_4)_2SO_4$ to a concentration of 300 mg/ml. The precipitate was collected by centrifugation and dissolved in 25 mM Na-acetate pH 5.0 (A-buffer). After dialysis, the sample was applied to a Q-sepharose column (Pharmacia Biotech AB, Uppsala, Sweden) equilibrated in A-buffer. The run-through was collected and applied directly to a SP-sepharose column (Pharmacia Biotech AB) also equilibrated in A-buffer. Bound enzyme was eluted by gradually increasing the concentration of NaCl to 1 M over 10 column volumes. Fractions containing pyranose oxidase activity were pooled and analyzed by SDS-PAGE. The major band has a molecular weight of approximately 65–70 kDa and an isoelectric point of 5.3.

Pyranose oxidase activity was assayed according to the following procedure: 180 µl D-glucose (500 mM) in 25 mM citrate-phosphate (each) pH 6.0 was mixed with 20 µl enzyme and incubated for 20 min at 30° C. An aliquot of 100 µl was combined with 100 µl of a solution consisting of 0.65 mM 2,2'-azinobis(3-ethylbenzthiazoline-6-sulphonic acid (ABTS) and 1.8 µg/ml recombinant *Coprinus cinerius* peroxidase (WO 95/10602). After 1 min the absorbance at 650 nm was measured. 0.1 mM $H_2O_2$ was used as an assay standard.

Example 2

Characterization of *T. hirsuta* Pyranose Oxidase

The temperature optimum was determined by measuring activity as described in Example 1 at different temperatures. The pH optimum was determined by changing the pH of the assay buffer in Example 1.

pH and temperature optima. The purified pyranose oxidase is active in the pH range of 3–9, with the highest activity at pH 6.0. The enzyme is active at temperatures up to 55° C. with a broad range (90%) of maximum activity between 30° C. and 50° C.

pH and temperature stability. The purified pyranose oxidase was incubated for 30 min at 50° C. at 7 different pH. The residual activity was subsequently determined by the assay described in example 1. No significant inactivation was observed in the pH range of 3–9, and more than 80% residual activity was retained at the end of the incubation period at all pH. The temperature dependent inactivation of the enzyme was further evaluated in a narrower range between 45 and 60° C. Pyranose oxidase was incubated in assay buffer at 45°, 50° and 55° C. Aliquots were withdrawn at 5, 10, 15, 20, 25 and 30 min and residual activity determined with the assay described above in Example 1. At 45° C. the enzyme remained stable during the entire incubation period. At 55° C. inactivation was slow and more than 50% residual activity was present after 30 min. At 60° C. an inactivation was observed with a half-time of inactivation ($t_{1/2}$) of 2–3 min in accordance with the observed temperature optimum.

Substrate specificity. To determine the specificity of the oxidase towards monosaccharides, D-glucose was substituted with various monosaccharides in the assay. All substrates were evaluated at a concentration of 500 mM. Table 1 summarizes the activity of the enzyme on various monosaccharides relative to D-glucose.

TABLE 1

Summary of substrate specificity of *T. hirsuta* pyranose oxidase

| Substrate | % Relative activity |
|---|---|
| D-Glucose | 100 |
| D-Xylose | 62.5 |
| D-Mannose | 51.1 |
| D-Galactose | 8.8 |
| β-D-Fructose | 4.6 |
| Methyl-α-D-glucopyranoside | 22.4 |
| Methyl-β-D-glucopyranoside | 59.6 |
| Sorbose | 91.4 |
| D-gluconic acid | 6.3 |
| 2-keto-D-gluconic acid | 0 |
| 5-keto-D-gluconic acid | 11.1 |
| 2-deoxy-D-glucose | 54.3 |

Example 3

Protein Sequencing and Amino Acid Analysis Methods

A highly purified preparation of *Trametes hirsuta* pyranose oxidase obtained as described above in Example 1 was reduced and alkylated. A sample of the enzyme was then degraded with Lys-C (WAKO pure chemicals industries Ltd., Japan). Peptides were isolated by RP-HPLC on a Vydac 218TP column (Vydac, U.S.A., Ca) in TFA (trifluoracetate)/acetonitrile and repurified on the Vydac 218TP column in TFA/isopropanol. Selected peptides were analyzed by Edman degradation.

The sequences obtained from five peptides and the N-terminal peptide are shown below in Table 2. The N-terminal sequence was determined by sequencing the purified enzyme electroblotted onto a PVDF membrane.

TABLE 2

Peptides obtained from a *Trametes hirsuta* pyranose oxidase

| Peptide name | Sequence |
|---|---|
| N-terminal | XLPPGMNVEYDVAIVGSGPIGXSYA |
| peptide 1 | NLFLGGCGNIPTAYXANPTLXA |
| peptide 2 | XVXDFQQIPLAFSRXSXTXVEXS |
| peptide 3 | LWFSDK |
| peptide 4 | HPDWWNEK |
| peptide 5 | FVXYPPAGQLP(L/V)PAGHNVFGEETRAVGXK |

Example 4 mRNA Isolation and cDNA Synthesis

Fermentation Procedure

*Trametes hirsuta* DSM2987 was inoculated from a plate with outgrown mycelium into a shake flask containing 100 ml medium B (30 g/l soya, 15 g/l maltodextrin, 5 g/l bacto peptone, 0.2 g/l pluronic). The culture was incubated at 26° C. for 5 days. The resulting culture broth was filtered through miracloth and the mycelia were stored in liquid nitrogen.

mRNA was isolated from mycelia from this culture as described by H. Dalboege et al (1994, Mol. Gen. Genet. 243:253–260), WO 93/11249 and WO 94/14953.

RNA Isolation

Total RNA was extracted from frozen mycelia using guanidinium thiocyanate followed by ultracentrifugation through a 5.7 M CsCl cushion. Isolation of poly(A)$^+$ RNA was carried out by oligo(dT)-cellulose affinity chromatography using the procedures described in WO 94/14953.

cDNA Synthesis

Double-stranded cDNA was synthesized from 5 mg poly (A)$^+$ RNA by the RNase H method (Gubler and Hoffman, 1983. Gene 25:263–269; Sambrook et al. (1989) Molecular cloning: A laboratory manual, Cold Spring Harbor lab., Cold Spring Harbor, N.Y). The poly(A)$^+$ RNA (5 µg in 5 µl of DEPC-treated water) was heated at 70° C. for 8 min. in a pre-siliconized, RNase-free microfuge tube, then quenched in ice. Reverse transcriptase buffer (50 mM Tris-Cl, pH 8.3, 75 mM KCl, 3 mM MgCl$_2$, 10 mM DTT; GIBCO-BRL, Life Technologies, Inc., Gaithersburg Md. U.S.A.) containing 1 mM of dATP, dGTP and dTTP, and 0.5 mM 5-methyl-dCTP (Pharmacia Biotech, Uppsala SE), 40 units human placental ribonuclease inhibitor (RNasin, Promega Corp., Madison Wis., U.S.A.), 1.45 µg of oligo(dT)$_{18}$-Not I primer (Pharmacia Biotech) and 1000 units SuperScript II RNase H reverse transcriptase (GIBCO-BRL) was added to the RNA for a final volume of 50 µl. First-strand cDNA was synthesized by incubating the reaction mixture at 45° C. for 1 hour. After synthesis, the mRNA:cDNA hybrid mixture was filtered through a MicroSpin S-400 HR spin column according to the manufacturer's instructions (Pharmacia Biotech).

The recovered hybrids were diluted in 250 µl second strand buffer (20 mM Tris-Cl, pH 7.4, 90 mM KCl, 4.6 mM MgCl$_2$, 10 mM (NH$_4$)$_2$SO$_4$, 0.16 mM bNAD+) containing 200 µl of each dNTP, 60 units *E. coli* DNA polymerase I (Pharmacia Biotech), 5.25 units RNase H (Promega Corp.) and 15 units *E. coli* DNA ligase (Boehringer Mannheim GmbH, Mannheim DE). Second strand cDNA synthesis was performed by incubating the reaction tube at 16° C. for 2 hours and an additional 15 min. at 25° C. The reaction was stopped by addition of EDTA to a final concentration of 20 mM followed by phenol and chloroform extractions.

Mung Bean Nuclease Treatment

The double-stranded cDNA was precipitated at –20° C. for 12 hours by addition of 2 vols 96% EtOH, 0.2 vol 10 M NH$_4$Ac, recovered by centrifugation, washed in 70% EtOH, dried and resuspended in 30 µl Mung bean nuclease buffer (30 mM NaAc, pH 4.6, 300 mM NaCl, 1 mM ZnSO$_4$, 0.35 mM DTT, 2% glycerol) containing 25 units Mung bean nuclease (Pharmacia Biotech). The single-stranded hair-pin DNA was clipped by incubating the reaction at 30° C. for 30 min., followed by addition of 70 µl 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-End Formation With T4 DNA Polymerase

The double-stranded cDNAs were recovered by centrifugation and resuspended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs, Beverly Mass., U.S.A.). The reaction mixture was incubated at 16° C. for 1 hour, and stopped by addition of EDTA to a final concentration of 20 mM, followed by phenol and chloroform extractions, and precipitation for 12 hours at –20° C. by adding 2 vols 96% EtOH and 0.1 vol 3 M NaAc pH 5.2.

Adaptor Ligation, Not I Digestion and Size Selection

After the fill-in reaction the cDNAs were recovered by centrifugation, washed in 70% EtOH and dried. The cDNA pellet was resuspended in 25 µl ligation buffer (30 mM Tris-Cl, pH 7.8, 10 mM MgCl$_2$, 10 mM DTT, 0.5 mM ATP) containing 2.5 µg non-palindromic BamHI adaptors and 30 units T4 ligase (Promega Corp.) and incubated at 16° C. for 12 hours. The reaction was stopped by heating at 65° C. for 20 min. and then cooling on ice for 5 min. The adapted cDNA was digested with Not I restriction enzyme by addition of 20 µl water, 5 µl 10× Not I restriction enzyme buffer (New England Biolabs) and 50 units enzyme (New England Biolabs), followed by incubation for 2.5 hours at 37° C. The reaction was stopped by heating at 65° C. for 10 min. The cDNAs were size-fractionated and purified from unligated adaptors and small cDNAs by gel electrophoresis on a 0.8% SeaPlaque GTG low melting temperature agarose gel (FMC Corp. Bioproducts, Rockland Ma., U.S.A.) in 1× TBE. The cDNA was size-selected with a cut-off at 0.7 kb and recovered from the gel by use of b-Agarase (New England Biolabs) according to the manufacturer's instructions and precipitated for 12 hours at –20° C. by adding 2 vols 96% EtOH and 0.1 vol 3 M NaAc pH 5.2.

Example 5

Construction of a cDNA Library

Plasmids

The Aspergillus expression vector pHD464 is derived from pMT1560, described in WO 94/23022. In order to clone a BamHI/NotI cDNA insert, a NotI site was introduced downstream from the BamHI site in the polylinker of pHD464.

Construction of cDNA Libraries

The directional, size-selected cDNA were recovered by centrifugation, washed in 70% EtOH, dried and resuspended in 30 µl 10 mM Tris-Cl, pH 7.5, 1 mM EDTA. The cDNAs were desalted through a MicroSpin S-300 HR spin column according to the manufacturer's instructions (Pharmacia Biotech). Three test ligations were carried out in 10 µl ligation buffer (30 mM Tris-Cl, pH 7.8, 10 mM MgCl$_2$, 10 mM DTT, 0.5 mM ATP) containing 5 µl double-stranded cDNA (reaction tubes #1 and #2), 15 units T4 ligase (Promega Corp.) and 30 ng (tube #1), 40 ng (tube #2) and 40 ng (tube #3, the vector background control BamHI-NotI cleaved pHD464 vector. The ligation reactions were performed by incubation at 16° C. for 12 hours, heating at 70° C. for 20 min. and addition of 10 μl water to each tube. One μl of each ligation mixture was electroporated into 40 μl electrocompetent *E. coli* DH10B cells (GIBCO-BRL) as described by Sambrook et al.

Using the optimal conditions a library was established in *E. coli* consisting of pools. Each pool was made by spreading transformed *E. coli* on LB+ampicillin agar plates giving 15.000–30.000 colonies/plate after incubation at 37° C. for 24 hours. Twenty ml LB+ampicillin was added to the plate and the cells were suspended herein. The cell suspension was shaken in a 50 ml tube for 1 hour at 37° C. Plasmid DNA was isolated from the cells according to the manufacturer's instructions using the QIAGEN plasmid kit and stored at −20° C. (Qiagen GmbH, Hilden DE).

Example 6

Identification of Pyranose Oxidase Clones

Approximately 10,000 *E. coli* DH10B colonies from cDNA library were screened by colony hybridization (Sambrook, et al., supra) using the random-primed $^{32}$P-labelled 615 bp PCR fragment amplified from the *Trametes hirsuta* cDNA obtained as described above in Example 5 (Oligolabbeling kit, Pharmacia Biotech) as the probe. The hybridization was carried out in 2×SSC, 5×Denhardt's solution, 0.5% SDS (w/v), 100 μg/ml denatured salomon sperm DNA for 20 h at 65° C. followed by two 15 min washes in 5×SSC at 25° C., two 30 min wash in 2×SSC, 0.5% SDS at 65° C., and two final 15 min washes in 5×SSC at 25° C. Eight colonies produced strong hybridization signals with the probe. The eight colonies were inoculated into five ml of Luria broth plus 50 μg/ml ampicillin medium and grown overnight at 37° C. Miniprep DNA was prepared from each of these clones using the Plasmid Mini Kit (Qiagen). A full length pyranose oxidase encoding sequence was identified in two of the clones, as confirmed by DNA sequencing.

Example 7

DNA Sequence Analysis of *Trametes hirsuta* Pyranose Oxidase Gene

Figure 1A:
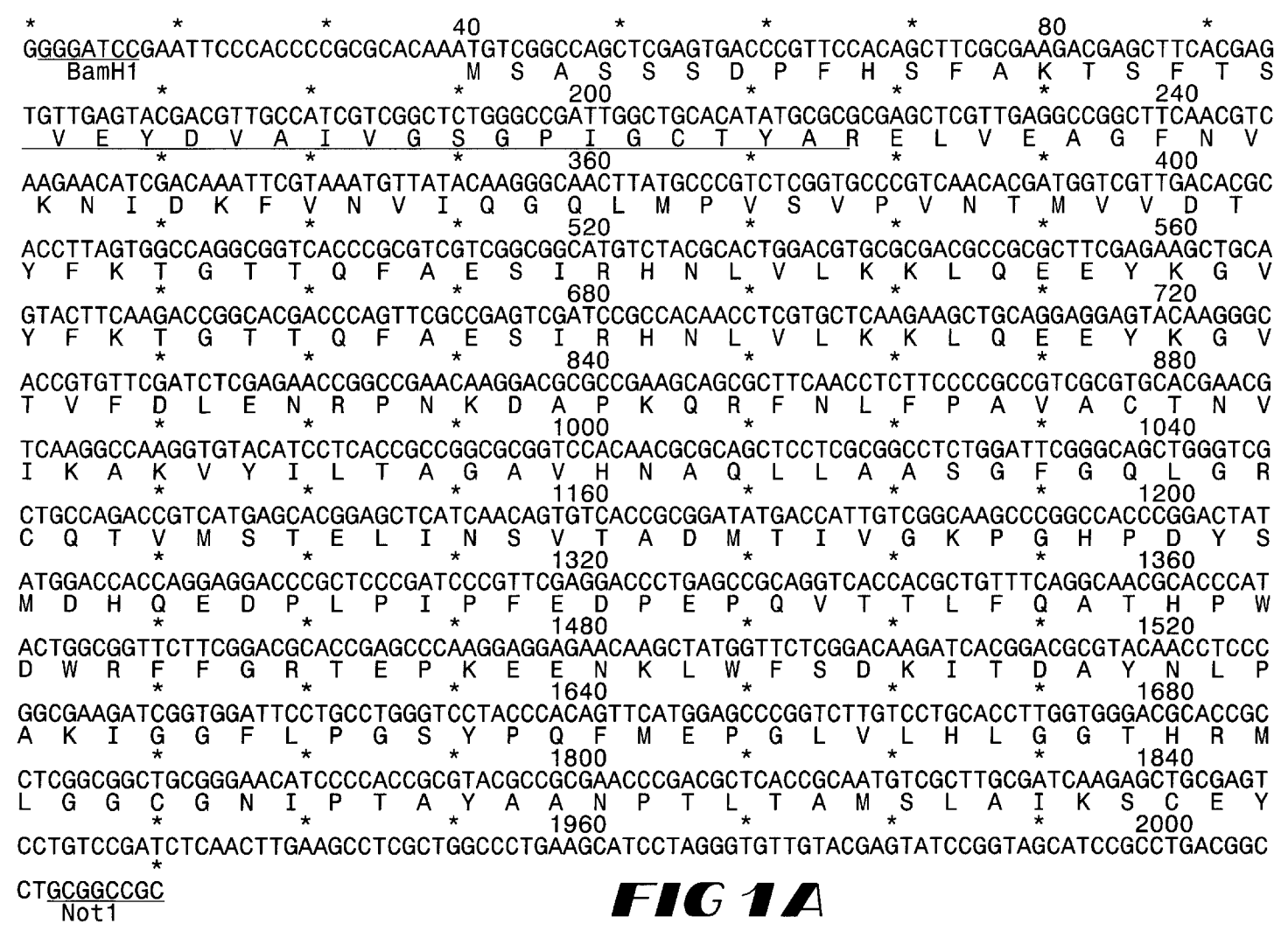

DNA sequencing of the two full length clones was performed using an Applied Biosystems Model 373A Automated DNA Sequencer (Applied Biosystems, Inc., Foster City, Calif.). Specific oligonucleotide sequencing primers were synthesized by T-A-G-Copenhagen ApS, Denmark. The nucleotide sequence of the gene encoding the *Trametes hirsuta* pyranose oxidase and the deduced amino acid sequence thereof is shown in FIG. 1 (SEQ ID NOS:1 and 2, respectively). Sequence analysis of the cloned insert revealed a large open reading frame of 1869 nucleotides (excluding the stop codon) encoding a protein of 622 amino acids sequence (SEQ ID NO:2). The G+C content of this open reading frame was determined to be 62.6%.

Based on the SignalP V1.1 prediction (Henrik Nielsen, Jacob Engelbrecht, Søren Brunak and Gunnar von Heijne, 1997. Identification of prokaryotic and eukaryotic signal peptides and prediction of their cleavage sites. Protein Engineering 10: 1–6), the first 27 amino acids probably comprise a secretory signal peptide which directs the nascent polypeptide into the endoplasmic reticulum (double underlined in FIG. 1). The sequence revealed homology of 82.2% to the coding sequence of *Coriolus versicolor* (DE 195 45 780) pyranose oxidase by GAP provided in the GCG program package (Program Manual for the Wisconsin Package, Version 8, August 1994, Genetics Computer Group, 575 Science Drive, Madison Wis., U.S.A.; Needleman, S. B. and Wunsch, C. D., 1970. Journal of Molecular Biology 48: 443–453) with the following settings for nucleotide sequence comparison: GAP creation penalty of 5.0 and GAP extension penalty of 0.3.

The amino acid sequences of the partial peptides derived from the purified aminopeptidase as described in Example 3 are underlined in FIG. 1 and are consistent with those found in the deduced amino acid sequence (SEQ ID NO:2) of the *Trametes hirsuta* pyranose oxidase cDNA.

Using the GAP program provided in the GCG program package (Program Manual for the Wisconsin Package, Version 8, August 1994, Genetics Computer Group, 575 Science Drive, Madison, Wis., U.S.A. 53711) (Needleman, S. B. and Wunsch, C. D., (1970), Journal of Molecular Biology, 48, 443–453 with the following settings for polypeptide sequence comparison: GAP creation penalty of 3.0 and GAP extension penalty of 0.1) to compare the deduced amino acid sequence of the *Trametes hirsuta* pyranose oxidase to that of *Coriolus versicolor* (DE 195 45 780), an identity of 82.5% was determined. The amino acid alignment between the pyranose oxidases from *Coriolus versicolor* and *Trametes hirsuta* is shown in FIG. 2.

Example 8

Expression of *Trametes hirsuta* Pyranose Oxidase
Transformation of *Aspergillus oryzae*

Protoplasts were prepared as described in WO 95/02043. One hundred μl of protoplast suspension was mixed with 5–25 μg of the appropriate DNA in 10 μl of STC (1.2 M sorbitol, 10 mM Tris-HCl, pH 7.5, 10 mM CaCl$_2$). Protoplasts were mixed with p3SR2 (an *A. nidulans* amdS gene carrying plasmid; Christensen, T., et al., 1988. Bio/Technology 6: 1419–1422) and incubated at room temperature for 25 minutes. Two hundred μl of 60% PEG 4000 (BDH 29576), 10 mM CaCl$_2$ and 10 mM Tris-HCl, pH 7.5 was added and carefully mixed, followed by adding and mixing in a second aliquot of 0.85 ml of the same solution and another 25 min incubation at room temperature. The mixture was centrifuged at 2500 g for 15 minutes and the pellet was resuspended in 2 ml of 1.2 M sorbitol. After a second sedimentation the protoplasts were spread on minimal plates (Cove, 1966. Biochem. Biophys. Acta 113: 51–56) containing 1.0 M sucrose, pH 7.0, 10 mM acetamide and 20 mM CsCl. After incubation for 4–7 days at 37° C. spores were picked and spread for single colonies. This procedure was repeated to obtain spores of a single colony, which were then stored as defined transformants.

Expression of *Trametes hirsuta* Pyranose Oxidase in *Aspergillus oryzae*

Because the cDNA library was constructed in the *A. oryzae* expression vector pHD464 as described above in Example 5, one of the full length clones obtained as described above in Example 6, pA2P.ox1, was transformed as described above directly into *A. oryzae* (WO 98/12300) by co-transformation with an amdS selection plasmid. The transformants were screened for pyranose oxidase activity in the supernatant using the assay procedure as described above in Example 1.

Deposit of Biological Materials

The following biological material has been deposited under the terms of the Budapest Treaty with the Deutsche Sammlung von Microorganismen und Zellkulteren GmbH (DSMZ), Mascheroder Weg 1b, D-38124 Braunschweig DE, and given the following accession number:

| Deposit | Accession Number | Date of Deposit |
|---|---|---|
| *Escherichia coli* DH10B + pA2P.ox1 | DSM 12119 | April 23, 1998 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated nucleic acid sequence encoding a polypeptide having pyranose oxidase activity, selected from the group consisting of:

(a) a nucleic acid sequence having at least 95% identity with the nucleic acid sequence of SEQ ID NO:1;

(b) a nucleic acid sequence encoding a polypeptide having an amino acid sequence which has at least 95% identity with the amino acid sequence of SEQ ID NO:2;

(c) a nucleic acid sequence which hybridizes under high stringency conditions with (i) the nucleic acid sequence of SEQ ID NO:1, or (ii) its complementary strand;

(d) an allelic variant of (a), (b), or (c); and (e) a subsequence of (a), (b), (c), or (d), wherein the subsequence encodes a polypeptide fragment which has pyranose oxidase activity.

2. The nucleic acid sequence of claim 1 which has the nucleic acid sequence of SEQ ID NO:1.

3. The nucleic acid sequence of claim 1, wherein the nucleic acid sequence encodes a polypeptide having pyranose oxidase activity obtained from Trametes.

4. The nucleic acid sequence of claim 3, wherein the nucleic acid sequence encodes a polypeptide having pyranose oxidase activity obtained from *Trametes hirsuta*, or a synonym or teleomorph thereof.

5. The nucleic acid sequence of claim 1 which encodes a polypeptide comprising the amino acid sequence of SEQ ID NO:2.

6. The nucleic acid sequence of claim 5, wherein the nucleic acid sequence encodes a polypeptide having pyranose oxidase activity obtained from Trametes.

7. The nucleic acid sequence of claim 6, wherein the nucleic acid sequence encodes a polypeptide having pyranose oxidase activity obtained from *Trametes hirsuta*.

8. The nucleic acid sequence of claim 1, which comprises the pyranose oxidase-encoding nucleic acid sequence contained in the plasmid pA2P.ox1 which is contained in *Escherichia coli* DSM 12119.

9. A nucleic acid construct comprising the nucleic acid sequence of claim 1 operably linked to one or more control sequences which direct the production of the polypeptide in a suitable expression host.

10. A recombinant expression vector comprising the nucleic acid construct of claim 9, a promoter, and transcriptional and translational stop signals.

11. The vector according to claim 10, further comprising a selectable marker.

12. A recombinant host cell comprising the nucleic acid construct of claim 9.

13. The cell according to claim 12, wherein the nucleic acid construct is contained on a vector.

14. The cell according to claim 12, wherein the nucleic acid construct is integrated into the host cell genome.

15. A method for producing a polypeptide having pyranose oxidase activity comprising (a) cultivating the host cell of claim 12 under conditions suitable for the production of the polypeptide; and (b) recovering the polypeptide.

16. An isolated nucleic acid sequence encoding a polypeptide having pyranose oxidase activity, selected from the group consisting of:

(a) a nucleic acid sequence having at least 90% identity with the nucleic acid sequence of SEQ ID NO:1;

(b) a nucleic acid sequence encoding a polypeptide having an amino acid sequence which has at least 90% identity with the amino acid sequence of SEQ ID NO:2; and (c) a nucleic acid sequence which hybridizes under high stringency conditions with (i) the nucleic acid sequence of SEQ ID NO:1, or (ii) its complementary strand.

* * * * *

SEQUENCE LISTING

<160> NUMBER OF SEQ ID NOS: 2

<210> SEQ ID NO 1
<211> LENGTH: 1869
<212> TYPE: DNA
<213> ORGANISM: Trametes hirsuta

<400> SEQUENCE: 1

```
atgtcggcca gctcgagtga cccgttccac agcttcgcga agacgagctt cacgagcaag      60
gctgcgaaga gggccactgc gcattctctc ccgccgctgc ctggtcccgg cgacctgccg     120
cctggtatga atgttgagta cgacgttgcc atcgtcggct ctgggccgat tggctgcaca     180
tatgcgcgcg agctcgttga ggccggcttc aacgtcgcca tgttcgagat tggagagatc     240
gactccggct tgaagatcgg ctcacacaag aagaacaccg tcgagtacca gaagaacatc     300
gacaaattcg taaatgttat acaagggcaa cttatgcccg tctcggtgcc cgtcaacacg     360
atggtcgttg acacgctaag cccggcgtca tggcaagctt cgacgttctt cgtccgcaac     420
ggggcgaatc cagagcaaga cccgctgcgc aaccttagtg gccaggcggt caccgcgtc      480 gtcggcggca tgtctacgca ctggacgtgc gcgacgccgc gcttcgagaa gctgcagcgc     540
ccgctgctcg tgaagaacga ctccaaggcg gacgacgccg agtgggacag gctctacaag     600
aaggccgagt cgtacttcaa gaccggcacg acccagttcg ccgagtcgat ccgccacaac     660
ctcgtgctca agaagctgca ggaggagtac aagggcgtgc gcgacttcca gcagatcccg     720
ctcgcggcga cgcgccagag cccgacgttc gtcgagtgga gctcggcgca caccgtgttc     780
gatctcgaga accggccgaa caaggacgcg ccgaagcagc gcttcaacct cttccccgcc     840
gtcgcgtgca cgaacgtgag gcgcgataac gcgaactcgg agatcgtagg cctggatgtc     900
cgcgacctcc acggggcgcaa gagcatcacc atcaaggcca aggtgtacat cctcaccgcc     960
ggcgcggtcc acaacgcgca gctcctcgcg gcctctggat tcgggcagct gggtcgtccc    1020 gacccgcca agccgctgcc gtctctgctg ccgtacctgg ggacccacat caccgagcag    1080
acgctcgtct tctgccagac cgtcatgagc acggagctca tcaacagtgt caccgcggat    1140
atgaccattg tcggcaagcc cggccacccg gactatagcg tcacgtatac cccgggcaac    1200
ccgaacaaca agcacccgga ctggtggaac gagaaggtga agaagcacat gatggaccac    1260
caggaggacc cgctcccgat cccgttcgag gaccctgagc cgcaggtcac cacgctgttt    1320
```

-continued

```
caggcaacgc acccatggca cacccagatt caccgcgacg ccttcagcta cggcgccgtg      1380
cagcagagca tcgactcgcg gctcatcgtc gactggcggt tcttcggacg caccgagccc      1440
aaggaggaga acaagctatg gttctcggac aagatcacgg acgcgtacaa cctccggcag      1500
ccgacgttcg acttccgctt ccccgggggc cgcgaagcgg aggacatgat gaccgacatg      1560
tgcgtcatgt cggcgaagat cggtggattc ctgcctgggt cctacccaca gttcatggag      1620
cccggtcttg tcctgcacct tggtgggacg caccgcatgg gcttcgacga gaaggcggac      1680
aagtgctgcg tcgacaccga ctcacgcgtc ttcggcttca agaacctctt cctcggcggc      1740
tgcgggaaca tccccaccgc gtacgccgcg aacccgacgc tcaccgcaat gtcgcttgcg      1800
atcaagagct gcgagtacat caagaagaac ttcgagccga gcccgaaccc cgtgaagcac      1860
cacaactag                                                             1869
```

```
<210> SEQ ID NO 2
<211> LENGTH: 622
<212> TYPE: PRT
<213> ORGANISM: Coriolus Versicolor

<400> SEQUENCE: 2

Met Ser Ala Ser Ser Asp Pro Phe His Ser Phe Ala Lys Thr Ser
  1               5                  10                  15

Phe Thr Ser Lys Ala Ala Lys Arg Ala Thr Ala His Ser Leu Pro Pro
             20                  25                  30

Leu Pro Gly Pro Gly Asp Leu Pro Pro Gly Met Asn Val Glu Tyr Asp
         35                  40                  45

Val Ala Ile Val Gly Ser Gly Pro Ile Gly Cys Thr Tyr Ala Arg Glu
     50                  55                  60

Leu Val Glu Ala Gly Phe Asn Val Ala Met Phe Glu Ile Gly Glu Ile
 65                  70                  75                  80

Asp Ser Gly Leu Lys Ile Gly Ser His Lys Lys Asn Thr Val Glu Tyr
                 85                  90                  95

Gln Lys Asn Ile Asp Lys Phe Val Asn Val Ile Gln Gly Gln Leu Met
            100                 105                 110

Pro Val Ser Val Pro Val Asn Thr Met Val Val Asp Thr Leu Ser Pro
        115                 120                 125

Ala Ser Trp Gln Ala Ser Thr Phe Phe Val Arg Asn Gly Ala Asn Pro
    130                 135                 140

Glu Gln Asp Pro Leu Arg Asn Leu Ser Gly Gln Ala Val Thr Arg Val
145                 150                 155                 160

Val Gly Gly Met Ser Thr His Trp Thr Cys Ala Thr Pro Arg Phe Glu
                165                 170                 175

Lys Leu Gln Arg Pro Leu Leu Val Lys Asn Asp Ser Lys Ala Asp Asp
            180                 185                 190

Ala Glu Trp Asp Arg Leu Tyr Lys Ala Glu Ser Tyr Phe Lys Thr
        195                 200                 205

Gly Thr Thr Gln Phe Ala Glu Ser Ile Arg His Asn Leu Val Leu Lys
    210                 215                 220

Lys Leu Gln Glu Glu Tyr Lys Gly Val Arg Asp Phe Gln Gln Ile Pro
225                 230                 235                 240

Leu Ala Ala Thr Arg Gln Ser Pro Thr Phe Val Glu Trp Ser Ser Ala
                245                 250                 255

His Thr Val Phe Asp Leu Glu Asn Arg Pro Asn Lys Asp Ala Pro Lys
            260                 265                 270
```

```
Gln Arg Phe Asn Leu Phe Pro Ala Val Ala Cys Thr Asn Val Arg Arg
        275                 280                 285

Asp Asn Ala Asn Ser Glu Ile Val Gly Leu Asp Val Arg Asp Leu His
        290                 295                 300

Gly Gly Lys Ser Ile Thr Ile Lys Ala Lys Val Tyr Ile Leu Thr Ala
305                 310                 315                 320

Gly Ala Val His Asn Ala Gln Leu Leu Ala Ala Ser Gly Phe Gly Gln
                325                 330                 335

Leu Gly Arg Pro Asp Pro Ala Lys Pro Leu Pro Ser Leu Leu Pro Tyr
            340                 345                 350

Leu Gly Thr His Ile Thr Glu Gln Thr Leu Val Phe Cys Gln Thr Val
            355                 360                 365

Met Ser Thr Glu Leu Ile Asn Ser Val Thr Ala Asp Met Thr Ile Val
        370                 375                 380

Gly Lys Pro Gly His Pro Asp Tyr Ser Val Thr Tyr Thr Pro Gly Asn
385                 390                 395                 400

Pro Asn Asn Lys His Pro Asp Trp Trp Asn Glu Lys Val Lys Lys His
                405                 410                 415

Met Met Asp His Gln Glu Asp Pro Leu Pro Ile Pro Phe Glu Asp Pro
            420                 425                 430

Glu Pro Gln Val Thr Thr Leu Phe Gln Ala Thr His Pro Trp His Thr
        435                 440                 445

Gln Ile His Arg Asp Ala Phe Ser Tyr Gly Ala Val Gln Gln Ser Ile
        450                 455                 460

Asp Ser Arg Leu Ile Val Asp Trp Arg Phe Phe Gly Arg Thr Glu Pro
465                 470                 475                 480

Lys Glu Glu Asn Lys Leu Trp Phe Ser Asp Lys Ile Thr Asp Ala Tyr
                485                 490                 495

Asn Leu Arg Gln Pro Thr Phe Asp Phe Arg Phe Pro Gly Gly Arg Glu
            500                 505                 510

Ala Glu Asp Met Met Thr Asp Met Cys Val Met Ser Ala Lys Ile Gly
            515                 520                 525

Gly Phe Leu Pro Gly Ser Tyr Pro Gln Phe Met Glu Pro Gly Leu Val
530                 535                 540

Leu His Leu Gly Gly Thr His Arg Met Gly Phe Asp Glu Lys Ala Asp
545                 550                 555                 560

Lys Cys Cys Val Asp Thr Asp Ser Arg Val Phe Gly Phe Lys Asn Leu
                565                 570                 575

Phe Leu Gly Gly Cys Gly Asn Ile Pro Thr Ala Tyr Ala Ala Asn Pro
            580                 585                 590

Thr Leu Thr Ala Met Ser Leu Ala Ile Lys Ser Cys Glu Tyr Ile Lys
        595                 600                 605

Lys Asn Phe Glu Pro Ser Pro Asn Pro Val Lys His His Asn
610                 615                 620
```